United States Patent [19]
Kurashima et al.

[11] Patent Number: 5,900,491
[45] Date of Patent: May 4, 1999

[54] PREPARATION PROCESS AND PURIFICATION PROCESS OF CYCLIC ESTER

[75] Inventors: Hideharu Kurashima; Yasushi Higuchi; Masahiro Kurokawa, all of Kanagawa-ken, Japan

[73] Assignee: Mitsubishi Gas Chemical Co., Inc., Tokyo, Japan

[21] Appl. No.: 08/934,638

[22] Filed: Sep. 22, 1997

[30] Foreign Application Priority Data

Oct. 4, 1996 [JP] Japan .................................. 8-264226

[51] Int. Cl.$^6$ ........................ C07D 319/06; C07D 319/12
[52] U.S. Cl. ............................................................. 549/274
[58] Field of Search .............................................. 549/274

[56] References Cited

U.S. PATENT DOCUMENTS

| | | | |
|---|---|---|---|
| 1,095,205 | 5/1914 | Grüter et al. . | |
| 2,668,162 | 2/1954 | Lowe | 260/78.3 |
| 4,797,468 | 1/1989 | De Vries | 528/354 |
| 5,053,522 | 10/1991 | Muller | 549/274 |

FOREIGN PATENT DOCUMENTS

| | | |
|---|---|---|
| 5-507076 | 10/1993 | Japan . |
| 6-504762 | 6/1994 | Japan . |
| 7-503490 | 4/1995 | Japan . |
| 7-504916 | 6/1995 | Japan . |
| 7-505150 | 6/1995 | Japan . |
| 7-309862 | 11/1995 | Japan . |
| WO 91/17986 | 11/1991 | WIPO . |
| WO 92/05167 | 4/1992 | WIPO . |
| WO 93/15127 | 8/1993 | WIPO . |
| WO 93/18020 | 9/1993 | WIPO . |
| WO 93/19058 | 9/1993 | WIPO . |

OTHER PUBLICATIONS

Takeshi Ito, "Production of Aliphatic Polyester", Abstract of JP 5–287056 A (Toyobo Co. Ltd.), Nov. 2, 1993.

Hiroshi Takayanagi, "Purification of Crude Glycollide", Abstract of JP 59–14877 A (Mitsui Toatsu Kagaku K.K.), Aug. 25, 1984.

Kamio Yonemoto, "Production of Unsaturated Dicarboxylic Acid Imide–Based Compound", Abstract of JP 3–223248 A (Matsushita Electric Works, Ltd.), Oct. 2, 1991.

Takeshi Ito, "Production of Aliphatic Polyester", Abstract of JP 6–287278 A (Toyobo Co., Ltd.), Oct. 11, 1994.

Seishi Hotta et al., "Production of Lactide", Abstract of JP 7–309862 A (Toyobo Co., Ltd.), Nov. 28, 1995.

Kazuomi Kubota, "Purification of Lactide", Abstract of JP 6–279435 A (Dainippon Ink & Chem., Inc.), Oct. 4, 1994.

Makoto Oguchi, "Method for Purifying Lactide and Method for Polymerizing the Same", Abstract of JP 7–118259 A (Shimadzu Corp.), May 9, 1995.

Makoto Oguchi, "Method for Purifying Lactide and Method for Polymerizing the Same", Abstract of JP 7–206851 A (Shimadzu Corp.), Aug. 8, 1995.

Chemical Abstracts, vol. 124, No. 23, 1996, Colombus, Ohio, US, abstract No. 317180r of JP 07–309–862 A, p. 1222.

*Primary Examiner*—Laura L. Stockton
*Attorney, Agent, or Firm*—Frishauf, Holtz, Goodman, Langer & Chick, P.C.

[57] ABSTRACT

A process for preparing a cyclic ester by reacting an α-hydroxycarboxylic acid or an α-hydroxycarboxyliclic acid ester with an orthoester. A process for purifying a cyclic ester by containing water and acid as impurities by adding an orthoester to a cyclic ester obtained by reaction of a reaction mixture including an α-hydrocarboxylic acid or an α-hydroxycarboxyliclic acid ester. According to the present invention, a high-purity cyclic ester containing small amounts of impurities such as water and an acid component can be provided.

19 Claims, No Drawings

PREPARATION PROCESS AND PURIFICATION PROCESS OF CYCLIC ESTER

BACKGROUND OF THE INVENTION

1. Field of the Invention

The present invention relates to a preparation process and a purification process of a cyclic ester typified by glycolide, lactide and tetramethyl glycolide. More specifically, it relates to a process for easily preparing a high-purity cyclic ester having extremely low contents of impurities such as an acid and water in a high yield by the use of an orthoester, and a process for purifying the cyclic ester.

2. Description of the Related Art

Cyclic esters typified by glycolide and lactide are cyclic dimers produced by the dehydration of two molecules of an α-hydroxycarboxyliclic acid or its ester, or by the removal of an alcohol therefrom, and they fall into the category of intramolecular cyclic esters. Thus, poly(α-hydroxycarboxyliclic acid esters) typified by poly(glycolic acid) and poly(lactic acid) obtained by the ring opening polymerization of these intramolecular cyclic esters have excellent biological degradation properties, so that they have been utilized as biologically degradable materials. In recent years, the problem of plastic wastes occurs owing to the shortage of garbage reclaiming lands and the incineration of the wastes, and so the poly(α-hydroxycarboxylic acid esters) are expected as biologically degradable plastics which can be degraded by hydrolysis, enzymes and microorganisms. In consequence, the demand and supply of these polyesters are gradually increasing.

In order to achieve a high molecular weight required for the biologically degradative materials and the biologically degradative plastics, it is necessary that the content of impurities such as an acid and water in a cyclic ester which is a starting material should be controlled to the lowest possible level, because such impurities disturb the attainment of the high molecular weight necessary to obtain sufficient physical properties. In the case of lactide, for example, it has been expected that the acid content is preferably 10 meg/kg or less, more preferably 5 meg/kg or less, and the water content is preferably 200 ppm or less, more preferably 100 ppm or less.

As a process for preparing a cyclic ester such as lactide of another α-hydroxycarboxyliclic acid or α-hydroxycarboxyliclic acid ester, there is usually a process for preparing the cyclic ester which comprises polymerizing a corresponding α-hydroxycarboxyliclic acid or α-hydroxycarboxyliclic acid ester to form a poly (hydroxycarboxylic acid) or a poly(hydroxycarboxylic acid ester) which is an oligomer, heating this oligomer up to about 200° C. in vacuum in the presence of a catalyst known in this technical field which is typified by stannous octanoate to decompose the same, whereby a cyclic dimer is obtained, and then distilling off the thus obtained cyclic ester (e.g., U.S. Pat. Nos. 1,095,205, 2,668,162, 4,797,468 and 5,053,522, Japanese Patent Application Laid-open Nos. 101378/1988 and 268179/1990, and Japanese PCT Patent Application Laid-open Nos. 503490/1995 and 505150/1995).

However, in the cyclic ester obtained by such a process, volatile impurities such as water and an acidic hydroxyl compound are included (refer to Comparative Example 3). Examples of these impurities usually include water, an α-hydroxycarboxyliclic acid monomer and oligomers of the α-hydroxycarboxyliclic acid. As described above, water and the carboxylic acids function as polymerization inhibitors during the polymerization of the cyclic ester, and they also deteriorate the storage stability of the cyclic ester. Therefore, the presence of these impurities is not preferable. Furthermore, Japanese PCT Patent Application Laid-open No. 503490/1995 and 505150/1995 have disclosed methods which comprise removing the hydroxyl impurities by redistillation to obtain the high-purity cyclic ester, but these methods have many disadvantageous points with respect of industrialization. For example, the yield of the cyclic ester which can be used as a polymer material deteriorates; the cyclic ester can scarcely possess such a quality as to be usable as the polymer material, even when the redistillation is done; operation is intricate; and facilities for the redistillation are additionally required (refer to Comparative Example 4).

In Japanese PCT Patent Application Laid-open No. 504916/1995, a process for preparing the cyclic ester from hydroxy acid and its derivative has been described, in which existing water is removed by the use of water getters such as acetic anhydride, an acetal and a carbodiimide in a step. However, these compounds have not been used in examples of the above-mentioned publication, and so the effect of the compounds is indefinite. Furthermore, in view of a fact that acetic acid is produced from acetic anhydride, the employment of acetic anhydride results in a reverse effect, instead of the reduction of an acid value. According to experiments of the acetal by the present inventors, the effect of the acid value reduction has not been observed (refer to Comparative Example 6). The carbodiimide has both the effects of the water removal and the acid value reduction, but since it contains a nitrogen atom, the carbodiimide causes the coloring of the cyclic ester, and it is also very expensive. For these reasons, it is difficult to industrially use the carbodiimide. Also in Japanese PCT Patent Application Laid-open No. 504762/1994, some water getters are referred to, but it is apparent that they also have the above-mentioned drawbacks.

In Japanese Patent Application Laid-open Nos. 287056/1993 and 287278/1994, a manufacturing process of an aliphatic polyester has been described which comprises polycondensing an α-hydroxycarboxyliclic acid in the presence of a primary alcohol, a carbodiimide or a polyhydric alcohol having 3 or more hydroxyl groups (a carboxyl group concentration adjustor) to form a precursor polymer having a carboxyl group concentration of 200 meg/kg or less, heating the precursor polymer to depolymerize it, and then subjecting the resulting cyclic ester to ring opening polymerization. Furthermore, Japanese Patent Application Laid-open No. 309862/1995 has described a process for preparing lactide which comprises dehydrocondensing lactic acid, to which a polyhydric alcohol having 3 or more hydroxyl groups has been added, in the presence of a metallic compound having the electronegativity of a metallic ion in the range of 10 to 15 to synthesize a precursor polymer having a carboxyl group concentration of 200 meg/kg or less, and heating this precursor polymer to depolymerize it. However, the cyclic ester (lactide) obtained by these methods also has some drawbacks. For example, the cyclic ester (lactide) does not possess such an acid value that it withstands a use as a polymer; the purity of the cyclic ester (lactide) is low and so a purification step is necessary for the use as the polymer; and the carboxyl group concentration adjustor and a substance formed by the modification of the adjustor with a reaction always remain in a reaction solution, which fact might cause the coloring of the obtained cyclic ester (lactide).

As techniques of purifying the cyclic ester, there are known recrystallization methods in which a sufficiently dried organic solvent such as toluene, ethyl acetate or isopropanol, or a mixed solvent is used (e.g., Japanese Patent Application Laid-open No. 101378/1988, Japanese PCT Patent Application Laid-open No. 507076/1993, and Japanese Patent Application Laid-open Nos. 279435/1994, 1,182,59/1995 and 2,068,51/1995; and as methods similar to the recrystallization methods, Japanese Patent Application Laid-open No. 165430/1988, and Japanese Patent Publication Nos. 25912/1990 and 15712/1993). The cyclic ester, from which the impurities for disturbing the polymerization have been removed by the recrystallization method and which has sufficiently been purified, can be used as a monomer for the polymerization, after subjected to steps such as filtration and drying. However, such a recrystallizing operation leads to the deterioration of the yield of the cyclic ester, makes the procedure intricate, and increases costs due to facilities required for the recrystallizing operation. Hence, the recrystallization methods have many disadvantageous points which make industrialization difficult.

Japanese Patent Application Laid-open No. 256340/1994 has suggested a purification process of lactide which comprises (1) cooling a molten mixture of lactide and impurities to the solidifying point of lactide or a little lower temperature than the solidifying point of lactide, (2) partially crystallizing the molten mixture to form a solid phase having a lower impurity content than the molten mixture and a liquid phase having a higher impurity content than the molten mixture, and (3) separating the solid phase from the liquid phase to collect the solid phase. This process has succeeded in obtaining lactide having an acid value of about 2 meq/g which can be used as a polymer material. However, this process also has some drawbacks. For example, temperature control is difficult in melting a solid lactide mixture and in cooling the molten mixture to the solidifying point of lactide; productivity is poor for reasons of a low zone movement rate and the like; and a facility cost increases uneconomically. Hence, this process has many disadvantageous points which make it difficult to actually industrialize the process.

In Japanese Patent Application Laid-open No. 223248/1991, a process for preparing an unsaturated dicarboxylic acid imide compound has been disclosed which comprises dehydrating an unsaturated dicarboxylic acid amide acid compound in the presence of an acid anhydride as a dehydrating agent, a basic catalyst and a metallic salt catalyst to close its ring, and then decomposing a secondarily produced acid with an orthoester into an alcohol and an ester to remove the acid, thereby obtaining the unsaturated dicarboxylic acid imide compound. However, in this publication, the preparation method of the unsaturated dicarboxylic acid imide compound is only described, and any description regarding the process for preparing the cyclic ester is not referred to therein.

SUMMARY OF THE INVENTION

As described above, a process for easily and inexpensively preparing or purifying a high-purity cyclic ester having an extremely low content of impurities such as an acid and water in a high yield has not been developed so far. The present invention has been investigated with the intention of solving the above-mentioned problems of conventional techniques, and an object of the present invention is to provide a process for easily and inexpensively preparing and purifying, in a high yield, a cyclic ester having a low acid value, a low water content and a high purity which can be used as a polymer material.

The present inventors have intensively investigated, and as a result, it has been found that the above-mentioned problems can be solved by adding an orthoester in the case that a cyclic ester is prepared by the use of an α-hydroxycarboxyliclic acid, an α-hydroxycarboxyliclic acid ester or a mixture thereof as a material, or in the case that the cyclic ester is purified. In consequence, the present invention has been attained.

That is to say, the first aspect of the present invention is directed to a preparation process of a cyclic ester by the use of an α-hydroxycarboxylic acid or an α-hydroxycarboxylic acid ester represented by the general formula $R^1R^2C(OH)COOR^3$ ($R^1$, $R^2$ and $R^3$ are each a hydrogen atom or an alkyl group having 1 to 6 carbon atoms) or a mixture thereof as a material, which comprises the step of adding an orthoester represented by the following general formula (I).

The second aspect of the present invention is directed to a purification process of a cyclic ester which comprises a step of adding an orthoester represented by the following general formula (I) to the cyclic ester obtained by the use of an α-hydroxycarboxyliclic acid or an α-hydroxycarboxyliclic acid ester represented by the general formula $R^1R^2C(OH)COOR^3$ ($R^1$, $R^2$ and $R^3$ are each a hydrogen atom or an alkyl group having 1 to 6 carbon atoms) or a mixture thereof as a material to convert an acid and water present in the cyclic ester into an alcohol and an ester, and a step of removing the formed alcohol and ester:

$$R^4C(OR^5)_3 \qquad (I)$$

wherein $R^4$ is a hydrogen atom or an alkyl group having 1 to 6 carbon atoms, and $R^5$ is an alkyl group having 1 to 6 carbon atoms, and $R^4$ and $R^5$ may be the same or different.

DESCRIPTION OF PREFERRED EMBODIMENTS OF THE INVENTION

Next, a process of the present invention will be described in detail. Examples of an α-hydroxycarboxyliclic acid or an α-hydroxycarboxyliclic acid ester which can be used as a raw material in the present invention include various compounds represented by the above-mentioned general formula $R^1R^2C(OH)COOR^3$, and typical examples thereof include glycolic acid, lactic acid, α-hydroxyisobutylic acid, methyl glycolate, ethyl glycolate, methyl lactate, ethyl lactate, butyl lactate, methyl α-hydroxyisobutylate and ethyl α-hydroxyisobutylate, but they are not restrictive. These raw materials can be used singly or in the form of a mixture of two or more kinds thereof. With regard to compounds including asymmetric carbon such as lactic acid and methyl lactate, all of a D-form, an L-form or a racemic form can be used. Furthermore, the state of them may be any of a solid, a liquid, an aqueous solution and a solution, but in the case that the aqueous solution is used, it is preferably concentrated prior to its use. A solvent can also be used, and examples of the solvent include aromatic hydrocarbons such as toluene, mixed xylene, o-xylene, m-xylene, p-xylene and ethylbenzene. These solvents can be used singly or in the form of a mixture of two or more kinds thereof. In the case that lactide is prepared, lactic acid and a lactic acid ester among the raw materials are used, but from the viewpoints of availability and manufacturing costs of the raw material and lactide, lactic acid and methyl lactate are preferable, and methyl lactate is particularly preferable, because a less amount of the orthoester is required when methyl lactate is employed. Moreover, in the case that tetramethyl glycolide is prepared, α-hydroxyisobutylic acid and an α-hydroxyisobutylic acid ester can be used, but from the viewpoints of availability and a manufacturing cost of tetramethyl glycolide, α-hydroxyisobutylic acid and methyl α-hydroxyisobutylateare preferable.

In the case that the lactic acid ester is used as the α-hydroxycarboxyliclic acid ester which is the raw material, a lactic acid ester produced by any of various methods can be employed, but it is industrially advantageous to use the lactic acid ester produced by a method comprising the following steps of (A) to (D).

Step (A): Lactonitrile is produced from prussic acid and acetaldehyde.

Step (B): Lactonitrile obtained by the previous step is hydrated to form lactamide.

Step (C): From lactamide obtained by the previous step and a formic acid ester presented by the general formula HCOOR (R is an alkyl group having 1 to 6 carbons), the lactic acid ester and formamide are formed.

Step (D): Formamide is separated from the products obtained in the previous step and then dehydrated to form prussic acid, and the thus formed prussic acid is recycled.

The lactic acid ester obtained by this method has characteristics that the secondary production of an ammonium salt which is observed in a conventional method is not involved at all and a free acid such as lactic acid is scarcely contained in the product. Therefore, the lactic acid ester obtained by this method can be used as material for producing lactide with advantage. Incidentally, this method has been disclosed in Japanese Patent Application Laid-open No. 233122/1995.

The orthoester which can be used in the process of the prevent invention can be presented by the general formula (1)

$$R^4C(OR^5)_3 \qquad (1)$$

wherein $R^4$ is a hydrogen atom or an alkyl group having 1 to 6 carbon atoms, and $R^5$ is an alkyl group having 1 to 6 carbon atoms, and they may be the same or different.

Examples of this orthoester include methyl orthoformate, ethyl orthoformate, propyl orthoformate, methyl orthoacetate, ethyl orthoacetate, propyl orthoacetate, methyl orthopropionate, ethyl orthopropionate, methyl orthoisopropionate, ethyl orthoisopropionate, methyl orthobutylate, ethyl orthobutylate, methyl orthoisobutylate and ethyl orthoisobutylate, but they are not specifically limited. These orthoesters preferably have a large boiling point difference between the orthoesters themselves and the obtained cyclic ester, and more preferably, they have a lower boiling point than the obtained cyclic ester. Examples of such orthoesters include methyl orthoformate, ethyl orthoformate, methyl orthoacetate and ethyl orthoacetate. These orthoesters can be used singly or in the form of a mixture of two or more kinds thereof. Furthermore, the orthoesters, when used, can be dissolved in an appropriate solvent or solution which can uniformly dissolve the same. In this connection, since these orthoesters are produced in an industrial scale, they are inexpensive and easily available.

In the preparation process of the present invention, the acid component and water that exist in at least one of the raw material, the reaction mixture, and the cyclic ester as the product (preferably, the cyclic ester obtained by the distillation) are converted into an alcohol and an ester with the above-mentioned orthoester. That is to say, in the process of the present invention, there can be taken (1) a way of adding the orthoester into the raw material before the reaction, (2) a way of adding the orthoester into the reaction mixture under the progress of the reaction (i.e., the reaction system), or (3) a way of adding the orthoester to the obtained cyclic ester after the completion of the reaction. Alternatively, the orthoester can dividedly be added at times of two or all of (1) before the reaction, (2) during the progress of the reaction, and (3) after the completion of the reaction.

In a preferable embodiment of the present invention, the acid and water present in the reaction mixture or the cyclic ester obtained by distillation are converted into an alcohol and an ester by the use of the orthoester, and the cyclic ester is then distilled or redistilled to obtain the cyclic ester containing extremely small amounts of the impurities. For example, in the case that the acid component is the α-hydroxycarboxyliclic acid (which is represented by $R^6COOH$) or an oligomer of the α-hydroxycarboxyliclic acid, a decomposition reaction by the orthoester is as follows:

$$R^6COOH + R^4C(OR^5)_3 \rightarrow R^6COOR^5 + R^4COOR^5 + R^5OH$$

Furthermore, in the case of water, the reaction is as follows:

$$H_2O + R^4C(OR^5)_3 \rightarrow R^4COOR^5 + 2R^5OH$$

As described above, the acid component and water are converted into an alcohol and an ester. The cyclic ester can be obtained as it is without removing them, but in general, it is preferable to remove them. No particular restriction is put on a technique for removing them, but the employment of distillation is preferable. The alcohol and the ester produced from the water and the acid component usually have lower boiling points than the original water and acid component, and hence it is very easy to remove them by the distillation. In the case that the starting material is the α-hydroxycarboxyliclic acid or the mixture of the α-hydroxycarboxyliclic acid and the α-hydroxycarboxyliclic acid ester, relatively large amounts of the acid component and water are present in any of the starting material, the reaction mixture and the cyclic ester obtained by the distillation, and therefore, in order to reduce the amount of the orthoester to be added as much as possible, a way may be taken in which the amounts of the acid component and water are beforehand decreased to some extent by the distillation or another means.

In preparing the cyclic ester, no particular restriction is put on the addition timing and the addition number of the orthoester. With regard to the addition timing, the orthoester can be added before the reaction as described above, during the reaction in which the dehydration and/or the alcohol removal of the material proceeds to some extent, immediately before the distillation of the cyclic ester, or at the time of the redistillation of the cyclic ester obtained by the distillation. In consideration of the easiness of the reaction operation, the necessary addition amount and the addition effect, it is preferable that the orthoester is added at one time immediately before the distillation of the cyclic ester or is added at one time before the redistillation of the cyclic ester obtained by the distillation without adding the orthoester.

No particular restriction is put on the amount of the orthoester to be added, but it depends on the kind of material, the addition timing of the orthoester and the like. In general, the amount of the orthoester to be added is in the range of 0.5 to 10.0 equivalents, preferably 1.0 to 5.0 equivalents of A shown in the following equation (II), which A means total value of an acid value and the water content of the material, the reaction mixture or the cyclic ester obtained by the distillation:

$$A = (\text{acid value [meq/kg]} + \text{water content [ppm]}/18) \qquad (II)$$

In consideration of the acid value, a water content reduction effect and cost, the amount of the orthoester is particularly preferably in the range of 1.1 to 3.0 equivalents of A. If the amount is less than 0.5 equivalent of A, the reduction effect of the acid value and the water content is poor, and on the other hand, if it is more than 10.0 equivalents of A, the cost increases uneconomically. If the material is the pure α-hydroxycarboxylic acid ester, the water content present in any of the reaction systems before, during and after the reaction is a negligible amount, and so the amount of the orthoester to be added can be decided on the basis of the acid value. In the case that the material is the α-hydroxycarboxylic acid or the mixture of the (α-hydroxycarboxylic acid and the α-hydroxycarboxyliclic acid ester, the acid component and the water content are naturally present in large quantities in any of the material, the reaction mixture and the cyclic ester obtained by the distillation. Accordingly, the required amount of the orthoester is greater than in the case that the α-hydroxycarboxyliclic acid ester is the material, and it must be decided in view of the acid value and the water content on the basis of the equation (II).

No particular restriction is put on a treatment temperature at a time when the added orthoester is reacted with the acid component and the water content, but the treatment temperature is preferably in the range of 25 to 300° C., more preferably 50 to 250° C., most preferably 100 to 200° C. If the treatment temperature is less than 25° C., a reaction rate is low and a treatment time is inconveniently long. On the other hand, if the treatment temperature is more than 300° C., secondary reactions are inconveniently liable to occur, which is not preferable, either. A pressure may be any of a reduced pressure, atmospheric pressure and an increased pressure, but the atmospheric or a slightly reduced atmospheric pressure is preferable. Moreover, the pressure may be constant or fluctuated. If desired, the treatment reaction can be carried out under an inert atmosphere, and in this case, a reactor is equipped with an inert gas introducing tube. Examples of the usable inert gas include nitrogen, helium, argon and carbon dioxide, but from an economical viewpoint, nitrogen is preferable. No particular restriction is put on a treatment reaction time, but it depends on the treatment temperature. Thus, the treatment reaction time is usually in the range of 0.1 to 10.0 hours, preferably 0.2 to 5.0 hours, more preferably 0.5 to 2.0 hours.

Furthermore, when the cyclic ester is prepared from the material by the addition of the orthoester, a catalyst can be used in any of the systems before the reaction, during the reaction of the dehydration and/or the alcohol removal, during the reaction of the added orthoester with the acid component and water, and during the redistillation in the case that the orthoester is added to the cyclic ester obtained by the distillation. Examples of the catalyst include inorganic acids such as sulfuric acid, hydrochloric acid, phosphoric acid and polyphosphoric acid, organic sulfonic acids such as benzenesulfonic acid, paratoluenesulfonic acid, methanesulfonic acid and trifluoromethanesulfonic acid, organic metallic compounds such as tetra-i-propyl titanate, titanium acetylacetonate, titanium lactate, tin (II) acetylacetonate, tin (II) methanesulfonate, tin (II) trifluoromethanesulfonate, dibutyltin dichloride, monobutyltin oxide, dimethyltin oxide, dibutyltin oxide, stannous octanoate and stannous oxalate, inorganic metallic compounds such as stannous oxide, stannous sulfate, stannous chloride and stannous diphosphate, solid acids such as strongly acidic cation exchange resins, zeolites (A type, X type, Y type, L type and ZSM-5), silica-alumina, silicatitania, bentonite, montmorillonite and active terra alba, and heteropoly-acids such as phosphomolybdic acid and phosphotungstic acid, and preferable examples thereof include paratoluenesulfonic acid, methanesulfonic acid, stannous octanoate, monobutyltin oxide and dibutyltin oxide.

These catalysts can be used singly or in the form of a mixture of two or more kinds thereof. No particular restriction is put on the amount of the catalyst, but it is preferably in the range of 0.01 to 5% by weight, more preferably 0.1 to 2% by weight based on the weight of the raw material. If the amount of the catalyst is less than 0.01% by weight, the effect of the catalyst is inconveniently insufficient, and for example, a reaction rate is low. On the other hand, if it is more than 5% by weight, the deterioration of selectivity and the increase of byproducts take place, and such a high ratio is also economically disadvantageous.

Since the cyclic ester prepared by the above-mentioned process contains extremely small amounts of impurities such as the acid component and water, it can directly be used as a polymer material or the like as it is. For example, in lactide which can usually be synthesized by using methyl lactate as the raw material in accordance with the process of the present invention, an acid value is 10 meq/kg or less and a water content was 100 ppm or less. This lactide is equal to or more excellent than lactide having an acid value of 1 to 5 meq/kg and a water content of 10 to 150 ppm conventionally obtained by redistillation or recrystallization (which is carried out several times on occasion, and a large labor is required), and this fact is surprising.

In the present invention, there is provided not only a process for preparing a cyclic ester containing small amounts of water and an acid component by adding an orthoester in the preparation step of the cyclic ester, but also a purification process for obtaining a cyclic ester containing small amounts of water and an acid component from a raw material, for example, a purchased cyclic ester containing large amounts of water and the acid component, or a cyclic ester in which the amounts of water and the acid component increase during a long-term storage. That is to say, the present invention is also directed to a purification process of a cyclic ester which comprises adding an orthoester represented by the general formula (I) to the cyclic ester to convert an acid and water present in the cyclic ester into an alcohol and an ester with the orthoester, and then removing the formed alcohol and ester:

$$R^4C(OR^5)_3 \qquad (I)$$

wherein $R^4$ is a hydrogen atom or an alkyl group having 1 to 6 carbon atoms, and $R^5$ is an alkyl group having 1 to 6 carbon atoms, and $R^4$ and R5 may be the same or different.

The purification process of the cyclic ester of the present invention can be carried out by all the same procedure as in the case that the orthoester is added at the time of the redistillation of the above-mentioned preparation process according to the present invention.

According to the present invention, there are provided a practical preparation process and purification process for obtaining a cyclic ester containing small amounts of impurities such as water and an acid component.

Next, the present invention will be described in more detail with reference to examples, but the scope of the present invention should not be limited by these examples.

Some characteristic values in the examples were measured in the following manners.

Measurement procedure of an acid value: In the case of a sample of a reaction mixture, about 1 g of the sample is weighed, or in the case of a sample of a cyclic ester, about 5 g of the sample is weighed, and the weighed sample is then dissolved in methylene chloride which has beforehand been desiccated by molecular sieves 3A (¹⁄₁₆ inch, made by Wako Pure Chemical Industries Co., Ltd.). Afterward, 10 drops of phenol red (0.05% by weight/volume in dry methanol)

which is an indicator for the decision of an end point are added to the sample solution. This solution is titrated with 0.025N potassium methoxide (a benzene.methanol solution) (which can be prepared by diluting, with dry methanol, 0.1 mol/potassium methoxide for non-aqueous titration made by Wako Pure Chemical Industries Co., Ltd.) to measure the acid value.

Conditions for gas chromatography analysis: A cyclic ester composition is analyzed. A cyclic ester is weighed, dissolved in tetrahydrofuran, and then analyzed. As a column, TC-17 (GL Science) is used. With regard to measurement conditions, an injection orifice temperature and an FID detector temperature are both set to 250° C., and a column temperature is raised from 60° C. to 240° C.

Measurement procedure of a water content: 1 g of a sample is dissolved in 5 g of methylene chloride, and the water content is then measured by the use of a water content measuring device (a trace water content measuring device CA-05 type, made by former Mitsubishi Chemical Industries, Ltd.).

EXAMPLE 1

Lactide Synthesis 1 from DL-methyl Lactate Material by Addition of Methyl Orthoformate (1) Alcohol Removal Step In a 500 ml flask equipped with a stirrer, a nitrogen introducing tube and a partial condenser were placed 416.4 g of DL-methyl lactate and 2.10 g of dibutyltin oxide (0.50% by weight based on the weight of methyl lactate), and reaction was started at a liquid temperature of 140° C. under a pressure of 600 mmHg, while nitrogen was blown thereinto. The temperature of the system was slowly raised up to 200° C. over 4.0 hours, while methanol produced by the polycondensation of methyl lactate was distilled off. Afterward, the pressure was gradually lowered to 200 mmHg over 1.0 hour. In consequence, 114.0 g of methanol was collected.

(2) Collection Step of Unreacted Methyl Lactate

The temperature was maintained at 200° C., and the pressure was slowly lowered to 10 mmHg over 1.0 hour to collect unreacted methyl lactate. Thus, 63.5 g of the collection containing 97.3% of methyl lactate was obtained.

(3) Methyl Orthoformate Addition and Initial Lactide Distillate Collection Step

The pressure in the reaction system was returned to atmospheric pressure by the use of nitrogen. The acid value of a reaction mixture was measured, and as a result, it was 32.0 meq/kg. Next, 2.46 g of methyl orthoformate was added (methyl orthoformate was added in an amount of 3.0 equivalents of the acid value of the reaction mixture, and the weight of the reaction mixture in the flask was calculated on the basis of the weight of collected methanol and collected methyl lactate), and the solution was then heated and stirred at a liquid temperature of 200° C. for 2.0 hours under a nitrogen gas stream. Afterward, the pressure was returned to 10 mmHg, and the initial distillate of lactide was distilled for 1 hour. The weight of the initial lactide distillate was 31.1 g, and it contained 19.9% of mesolactide and 14.2% of DL-lactide.

(4) Lactide Distillation Step

The temperature was raised up to 210° C. and the pressure was maintained at 5 mmHg, and the reaction solution obtained in the above paragraph (3) was then distilled to obtain 210.1 g of lactide as a main distillate. The thus obtained lactide had a purity of 99.4% (meso-23 lactide= 43.0%, DL-lactide=56.4%), an acid value of 7.2 meq/kg and a water content of 20 ppm.

EXAMPLE 2

Lactide Synthesis 2 from DL-methyl Lactate Material by Addition of Methyl Orthoformate The operation of reaction was conducted by the same procedure as in Example 1 except that the amount of methyl orthoformate in the step (3) of Example 1 was 1.1 equivalents of an acid value, thereby obtaining 214.8 g of lactide. The thus obtained lactide had a purity of 99.2% (mesolactide=43.1%, DL-lactide=56.1%), an acid value of 13.7 meq/kg and a water content of 25 ppm.

EXAMPLE 3

Lactide Synthesis 3 from DL-methyl Lactate Material by Addition of Methyl Orthoformate The operation of reaction was conducted by the same procedure as in Example 1 except that the amount of methyl orthoformate in the step (3) of Example 1 was 5.0 equivalents of an acid value, thereby obtaining 220.2 g of lactide. The thus obtained lactide had a purity of 99.3% (mesolactide=41.8%, DL-lactide=57.5%), an acid value of 2.5 meq/kg and a water content of 20 ppm.

EXAMPLE 4

Lactide Synthesis from DL-methyl Lactate Material by Addition of Methyl Orthoformate The operation of reaction was conducted by the same procedure as in Example 1 except that methyl orthoformate in the step (3) of Example 1 was replaced with ethyl orthoformate, thereby obtaining 219.4 g of lactide. The thus obtained lactide had a purity of 99.2% (mesolactide lactide= 41.3%, DL-lactide=57.9%), an acid value of 5.1 meq/kg and a water content of 25 ppm.

EXAMPLE 5

Lactide Synthesis from DL-methyl Lactate Material by Addition of Methyl Orthoformate The operation of reaction was conducted by the same procedure as in Example 1 except that methyl orthoformate in the step (3) of Example 1 was replaced with methyl orthoacetate, thereby obtaining 215.5 g of lactide. The thus obtained lactide had a purity of 99.5% (mesolactide=42.7%, DL-lactide=56.8%), an acid value of 6.9 meq/kg and a water content of 30 ppm.

EXAMPLE 6

Lactide Synthesis from DL-methyl Lactate Material by Addition of Methyl Orthoformate The operation of reaction was conducted by the same procedure as in Example 1 except that DL-methyl lactate in the step (1) of Example 1 was replaced with Lmethyl lactate, thereby obtaining 218.2 g of lactide. The thus obtained lactide had a purity of 99.1% (mesolactide=3.9%, L-lactide= 95.2%), an acid value of 4.6 meq/kg and a water content of 30 ppm.

COMPARATIVE EXAMPLE 1

Lactide Synthesis from DL-methyl Lactate Material

The operation of reaction was conducted by the same procedure as in Example 1 except that the addition of methyl orthoformate in the step (3) of Example 1 was omitted, thereby obtaining 217.6 g of lactide. The thus obtained lactide had a purity of 99.0% (mesolactide=44.0%, DL-lactide=55.0%), an acid value of 30.7 meq/kg and a water content of 40 ppm.

COMPARATIVE EXAMPLE 2

Redistillation of Lactide Obtained in Comparative Example 1

Lactide obtained in Comparative Example 1 was redistilled at a liquid temperature of 135° C. under a pressure of 5 mmHg, thereby obtaining 185.2 g of purified lactide (85% by weight of unredistilled lactide). The thus obtained lactide had a purity of 99.9% (mesolactide 40.2%, DL-lactide= 59.7%), an acid value of 1.42 meq/kg and a water content of 30 ppm.

EXAMPLE 7

Redistillation of Lactide Obtained by the Same Reaction Procedure as in Comparative Example 1 by Addition of Methyl Orthoformate The operation of reaction was conducted by the same procedure as in Comparative Example 1 to obtain 224.2 g of lactide. The thus obtained lactide had a purity of 99.0% (mesolactide=43.0%, DL-lactide=56.0%), an acid value of 29.8 meq/kg and a water content of 45 ppm. To obtained lactide, 2.31 g of methyl orthoformate (3.0 times as much as the total equivalent of the acid value and the water content) was added, followed by heating and stirring at a liquid temperature of 150° C. for 2.0 hours under a nitrogen gas stream. Afterward, the solution was redistilled at a liquid temperature of 135° C. under a pressure of 5 mmHg, thereby obtaining 192.8 g of purified lactide (86% by weight of unredistilled lactide). The thus obtained lactide had a purity of 99.9% or more (mesolactide=40.2%, DL-lactide=59.7%), an acid value of 1.5 meq/kg and a water content of 20 ppm.

EXAMPLE 8

Redistillation of Lactide Obtained in Example 1 by Addition of Methyl Orthoformate To lactide obtained in Example 1, 0.56 g of methyl orthoformate (3.0 times as much as the total equivalent of an acid value and a water content) was added, followed by heating and stirring at a liquid temperature of 150° C. for 2.0 hours under a nitrogen gas stream. Afterward, the solution was redistilled at a liquid temperature of 135° C. under a pressure of 5 mmHg, thereby obtaining 182.8 g of purified lactide (87% by weight of unredistilled lactide). The thus obtained lactide had a purity of 99.9% or more (mesolactide=43.4%, DL-lactide=56.5%), an acid value of 0.8 meq/kg and a water content of 15 ppm.

EXAMPLE 9

Lactide Synthesis from DL-methyl Lactate Material by Recycling Initial Lactide Distillate and Residue and by Addition of Methyl Orthoformate The operation of reaction was conducted by the same procedure as in Example 1 to obtain 45.8 g (including 95.0% of methyl lactate), 20.8 g of an initial lactide distillate (including 14.3% of methyl lactate, 13.2% of methyl lactoyllactate, 40.4% of mesolactide and 29.0% of DL-lactide), 222.2 g of lactide and 25.7 g of a residue. Next, to this residue, there were added 365.3 g of DL-methyl lactate, 43.2 g of recovered methyl lactate, 18.8 g of an initial lactide distillate and 1.05 g of dibutyltin oxide, and the same reaction as in Example 1 was carried out to obtain 228.4 g of lactide. The thus obtained lactide had a purity of 99.0% (mesolactide=38.7%, DL-lactide=60.3%), an acid value of 8.9 meq/kg and a water content of 30 ppm.

EXAMPLE 10

Lactide Synthesis from DL-lactic Acid Material by Addition of Methyl Orthoformate In the same device as in Example 1 were placed 447.4 g of an aqueous DL-lactic acid (85–92%) solution and 4.06 g of dibutyltin oxide, followed by concentration at a liquid temperature of 150° C. under atmospheric pressure for 0.5 hour. Next, while the pressure was gradually reduced to 15 mmHg, the temperature was raised up to 200° C., whereby a lactic acid oligomer was produced for 8.0 hours. At this time, 127.5 g of distilled water was obtained. The pressure in the reaction system was returned to atmospheric pressure by the use of nitrogen, and an acid value and a water content of the reaction mixture were measured. As a result, the acid value was 280 meq/kg, and the water content was 2020 ppm. 40.5 g of methyl orthoformate (3.0 times as much as the total equivalent of the acid value and the water content) was added, and the solution was heated and stirred at a liquid temperature of 200° C. for 2.0 hours, while nitrogen was blown thereinto. The distillation of lactide was carried out at a liquid temperature of 210° C. under a pressure of 5 mmHg for 5.0 hours to obtain 247.6 g of lactide. The thus obtained lactide had a purity of 98.2% (mesolactide=39.6%, DL-lactide=58.6%), an acid value of 10.0 meq/kg and a water content of 75 ppm.

COMPARATIVE EXAMPLE 3

Lactide Synthesis from DL-lactic Acid Material

The operation of reaction was conducted by the same procedure as in Example 10 except that the addition of methyl orthoformate in Example 10 was omitted, thereby obtaining 250.2 g of lactide. The thus obtained lactide had a purity of 95.8% (mesolactide=41.8%, DL-lactide=54.0%), an acid value of 380 meq/kg and a water content of 455 ppm.

COMPARATIVE EXAMPLE 4

Redistillation of Lactide Obtained in Comparative Example 3

Lactide Obtained in Comparative Example 3 was redistilled at a liquid temperature of 135° C. under a pressure of 5 mmHg, thereby obtaining 200.2 g of purified lactide (80% by weight of unredistilled lactide). The thus obtained lactide had a purity of 98.1% (mesolactide=40.4%, DL-lactide=57.7%), an acid value of 75.3 meq/kg and a water content of 150 ppm.

EXAMPLE 11

Redistillation of Lactide Obtained by the Same Reaction Procedure as in Comparative Example 3 by Addition of Methyl Orthoformate The operation of reaction was conducted by the same procedure as in Comparative Example 3 to obtain 249.8 g of lactide. The thus obtained lactide had a purity of 96.2% (mesolactide=42.5%, DL-lactide=53.7%), an acid value of 365 meq/kg and a water content of 470 ppm. To the obtained lactide, 31.1 g of methyl orthoformate (3.0 times as much as the total equivalent of the acid value and the water content) was added, and the solution was heated and stirred at a liquid temperature of 150° C. for 2.0 hours, while nitrogen was blown thereinto. Afterward, the solution was redistilled at a liquid temperature of 135° C. under a pressure of 5 mmHg, thereby obtaining 209.8 g of purified lactide (84% by weight of unredistilled lactide). The thus obtained lactide had a purity of 99.7% or more (mesolactide=42.7%, DL-lactide= 57.0%), an acid value of 4.2 meq/kg and a water content of 35 ppm.

EXAMPLE 12

Redistillation of Lactide Obtained in Example 10 by Addition of Methyl Orthoformate 1.12 g of methyl orthoformate (3.0 times as much as the total equivalent of an acid value and a water content) was added to lactide obtained in Example 10, followed by heating and stirring at a liquid temperature of 150° C. for 2.0 hours under a nitrogen gas stream. Afterward, the solution was redistilled at a liquid temperature of 135° C. under a pressure of 5 mmHg, thereby obtaining 208.0 g of purified lactide (84% by weight of unredistilled lactide). The thus obtained lactide had a purity of 99.8% or more (mesolactide=41.9%, DL-lactide=57.9%), an acid value of 2.9 meq/kg and a water content of 30 ppm.

EXAMPLE 13

Lactide Synthesis from L-lactic Acid Material by Addition of Methyl Orthoformate The operation of reaction was conducted by the same procedure as in Example 10 except that DL-lactic acid in Example 10 was replaced with L-lactic acid, thereby obtaining 252.2 g of lactide. The thus obtained lactide had a purity of 98.4% (mesolactide=6.3%, L-lactide=92.1%), an acid value of 8.9 meq/kg and a water content of 30 ppm.

COMPARATIVE EXAMPLE 5

Lactide Synthesis from L-lactic Acid Material

The operation of reaction was conducted by the same procedure as in Example 13 except that the addition of methyl orthoformate in Example 13 was omitted, thereby obtaining 243.1 g of lactide. The thus obtained lactide had a purity of 96.3% (mesolactide=39.1%, DL-lactide=57.2%), an acid value of 325 meq/kg and a water content of 495 ppm.

COMPARATIVE EXAMPLE 6

Lactide Synthesis from DL-methyl Lactate Material by Addition of 1,1-dimethoxycyclohexane The operation of reaction was conducted by the same procedure as in Example 1 except that methyl orthoformate in Example 1 was replaced with 1,1-dimethoxycyclohexane, thereby obtaining 218.9 g of lactide. The thus obtained lactide had a purity of 99.1% (mesolactide=42.5%, DL-lactide=56.6%), an acid value of 38.2 meq/kg and a water content of 40 ppm.

EXAMPLE 14

Tetramethyl Glycolide Synthesis from Methyl α-hydroxyisobutylatematerial by Addition of Methyl Orthoformate at Distillation In a flask (1 liter) equipped with a stirrer, a partial condenser, a reflux condenser and a water separator were placed 295.3 g of methyl α-hydroxyisobutylate, 20.0 g of methanesulfonic acid (a 70 wt % aqueous solution) and 82.0 g of water, and reaction was then carried out for 6 hours by heating the solution to 110° C., while methanol secondarily produced by hydrolysis was distilled off. After the reaction solution was cooled, 520.6 g of metaxylene was added to the flask, and reaction was then carried out for 12 hours by heating the solution under reflux, while water was removed by the water separator. Next, the solvent was distilled off from the solution under reduced pressure, and with the progress of concentration, crystals of crude tetramethyl glycolide precipitated. Crude tetramethyl glycolide had an acid value of 250 meq/kg and a water content of 650 ppm. 19.6 g of methyl orthoformate (3.0 times as much as the total equivalent of the acid value and the water content, on the assumption that a theoretical amount of tetramethyl glycolide was produced) was added, and the solution was heated and stirred at a liquid temperature of 150° C. for 2.0 hours, while nitrogen was blown thereinto. Afterward, crude tetramethyl glycolide was distilled at a liquid temperature of 120° C. under a pressure of 10 mmHg, thereby obtaining 170.2 g of tetramethyl glycolide. The thus obtained tetramethyl glycolide had a purity of 99.9%, an acid value of 8.9 meq/kg and a water content of 30 ppm.

COMPARATIVE EXAMPLE 7

Tetramethyl Glycolide Synthesis from Methyl α-hydroxyisobutylatematerial

In a flask (1 liter) equipped with a stirrer, a partial condenser, a reflux condenser and a water separator were placed 295.3 g of methyl α-hydroxyisobutylate, 20.0 g of methanesulfonic acid (a 70 wt % aqueous solution) and 82.0 g of water, and reaction was then carried out for 6 hours by heating the solution to 110° C., while methanol secondarily produced by hydrolysis was distilled off. After the reaction solution was cooled, 520.6 g of metaxylene was added to the flask, and reaction was then carried out for 12 hours by heating the solution under reflux, while water was removed by the water separator. Next, 30.8 g of a sodium carbonate powder was added to the cooled reaction solution, and the solution was then neutralized with stirring, until a pH of about 4 was reached. The solvent was distilled off from the solution under reduced pressure, and with the progress of concentration, crystals of crude tetramethyl glycolide precipitated. Remaining crude tetramethyl glycolide was distilled at a liquid temperature of 120° C. under a pressure of 10 mmHg to obtain 155.0 g of tetramethyl glycolide. The obtained tetramethyl glycolide had a purity of 99.8%, an acid value of 40.3 meq/kg and a water content of 95 ppm.

EXAMPLE 15

Tetramethyl Glycolide Synthesis from α-hydroxyisobutylic Acid Material by Addition of Methyl Orthoformate at distillation In a flask (1 liter) equipped with a stirrer, a partial condenser, a reflux condenser and a water separator were placed 260.3 g of α-hydroxyisobutylic acid, 520.6 g of metaxylene and 20.0 g of methanesulfonic acid (a 70 wt % aqueous solution), and reaction was then carried out for 12 hours by heating the solution under reflux, while water was removed by the water separator. Next, the solvent was distilled off from the solution under reduced pressure, and with the progress of concentration, crystals of crude tetramethyl glycolide precipitated. Crude tetramethyl glycolide had an acid value of 325 meq/kg and a water content of 725 ppm. 25.0 g of methyl orthoformate (3.0 times as much as the total equivalent of the acid value and the water content, on the assumption that a theoretical amount of tetramethyl glycolide was produced) was added, and the solution was heated and stirred at a liquid temperature of 150° C. for 2.0 hours, while nitrogen was blown thereinto. Afterward, crude tetramethyl glycolide was distilled at a liquid temperature of 120° C. under a pressure of 10 mmHg, thereby obtaining 177.8 g of tetramethyl glycolide. The thus obtained tetramethyl glycolide had a purity of 99.9%, an acid value of 9.7 meq/kg and a water content of 35 ppm.

COMPARATIVE EXAMPLE 8

Tetramethyl Glycolide Synthesis from α-hydroxyisobutylic Acid Material

In a flask (1 liter) equipped with a stirrer, a partial condenser, a reflux condenser and a water separator were placed 260.3 g of α-hydroxyisobutylic acid, 520.6 g of metaxylene and 20.0 g of methanesulfonic acid (a 70 wt % aqueous solution), and reaction was then carried out for 12 hours by heating the solution under reflux, while water was removed by the water separator. Next, 30.8 g of a sodium carbonate powder was added to the cooled reaction solution, and the solution was then neutralized with stirring, until a pH of about 4 was reached. The solvent was distilled off from the solution under reduced pressure, and with the progress of concentration, crystals of crude tetramethyl glycolide precipitated. Remaining crude tetramethyl glycolide was distilled at a liquid temperature of 120° C. under a pressure of 10 mmHg to obtain 162.2 g of tetramethyl glycolide. The obtained tetramethyl glycolide had a purity of 99.8%, an acid value of 35.6 meq/kg and a water content of 100 ppm.

EXAMPLE 16

Purification of DL-lactide by Addition of Methyl Orthoformate 0.81 g of methyl orthoformate (3.0 times as much as the total equivalent of an acid value and a water content) was added to 100 g of a reagent DL-lactide (having an acid value of 21.8 meq/kg and a water content of 65 ppm, made by Tokyo Chemical Industry Co., Ltd.), followed by heating and stirring at a liquid temperature of 150° C. for 2.0 hours under a nitrogen gas stream. Afterward, the solution was redistilled at a liquid temperature of 135° C. under a pressure of 5 mmHg, thereby obtaining 86 g of purified DL-lactide. The obtained DL-lactide had a purity of 99.9% or more, an acid value of 1.1 meq/kg and a water content of 25 ppm.

SYNTHETIC EXAMPLE

Synthesis of Methyl Lactate

Step (A): Synthesis of Lactonitrile from Prussic Acid and Acetaldehyde

In a 500 ml flask equipped with a stirrer, a thermometer, a reflux condenser and a dropping funnel were placed 88.1 g of acetaldehyde and 1 ml of a 1N aqueous sodium hydroxide solution, and 59.4 g of prussic acid was added dropwise thereto, the temperature in the flask being maintained at 10° C. After the completion of the prussic acid dropping, a temperature of 20° C. was maintained for 2 hours to bring the reaction to an end. Next, 50% sulfuric acid was added to adjust the pH of the formed solution to 3. The flask was connected to a vacuum system, whereby unreacted prussic acid was removed from the reaction system to obtain 142 g of lactonitrile. The thus obtained lactonitrile had a purity of 98.8%, and a yield of lactonitrile based on acetaldehyde was 98.7%.

Step (B): Synthesis of Lactoamide by Hydration of Lactonitrile

Preparation of a catalyst: In a 1 liter flask equipped with a stirrer, a reflux condenser and a thermometer were placed 63.2 g of potassium permanganate and 500 g of water, followed by heating to 70° C. and stirring. Further, 240 g of an aqueous solution containing 96.2 g of dissolved manganese sulfate, and 40 g of 15% sulfuric acid were added thereto, and reaction was then carried out at 70° C. for 3 hours. After the contents were cooled, the precipitate was filtered with suction, and then washed with 2.4 liters of water. The resulting precipitate cake was dried at 60° C. overnight to obtain 74 g of active manganese dioxide, which was used as the undermentioned catalyst.

Hydration reaction: In a 1 liter flask equipped with a stirrer, a reflux condenser and a thermometer were placed 121 g of lactonitrile obtained in the step (A), 350 g of water and 60 g of manganese dioxide in turn, and reaction was then carried out by heating and stirring the solution at 60° C. for 5 hours. After cooled on ice, the formed solution was filtered with suction to separate the catalyst. The filtrate was analyzed by gas chromatography, and as a result, it was apparent that the conversion of lactonitrile was 99.5% and the yield of lactoamide were 97.5%. This filtrate was concentrated to dryness under reduced pressure to obtain 148 g of lactoamide having a purity of 99.5% or more as a main component.

Step (C): Synthesis of Methyl Lactate and Formamide from Lactoamide and Methyl Formate In a 1 liter stainless steel autoclave equipped with a stirrer were placed 44.5 g of lactoamide obtained in the step (B), 180 g of methyl formate, 96 g of methanol and 1.1 g of sodium methoxide, and reaction was then carried out by heating and stirring the solution at 60° C. for 2 hours. After cooled, the resulting product was analyzed by gas chromatography, and as a result, it was apparent that the conversion of lactoamide was 86.1%, the selectivity of methyl lactate based on lactoamide was 99.8%, and the selectivity of formamide was 98.4%. After sodium methoxide in the formed solution was neutralized with sulfuric acid, the solution was distilled in an ordinary manner to recover methyl formate and methanol and simultaneously to obtain 40 g of methyl lactate having a purity of 99% or more and 14 g of formamide having a purity of 99% or more. A recovery ratio of the recovered materials inclusive of intermediate fractions was quantitative.

Step (D): Preparation of Prussic Acid by Dehydration of Formamide

Preparation of a catalyst: 0.88 g of sodium carbonate dissolved in 30 g of water was added to 51.5 g of manganese carbonate, followed by kneading for 1 hour. Afterward, the kneaded material was dried at 110° C. for 15 hours, calcined at 450° C. for 5 hours under a 10% hydrogennitrogen gas stream, and then ground to obtain 30 g of the particles having a uniform size of 10 to 20 mesh.

Reaction: 3.0 g of manganese oxide obtained in the above-mentioned manner was filled into a quartz reaction tube having an inner diameter of 10×300 mm and equipped with a thermometer sheath tube, and the reaction tube was heated so that the temperature of the lower portion of a catalyst layer might be maintained at 400° C. Furthermore, a 15 cm-height upper portion of the catalyst layer was filled with quarts Raschig rings having a size of 3×3 mm, and then heated to 100 to 400° C. to form a formamide evaporating portion. While the vacuum degree in the reaction tube was maintained at 100 mmHg, formamide obtained in the step (C) and air were introduced into the system through the top portion of the reaction tube at ratios of 10 g/hr and 240 ml/hr, respectively. From a time when 5 hours had lapsed after the start of the reaction, a reaction gas was sampled for 1 hour. Prussia acid collected by allowing water and an aqueous NaOH solution to absorb it was determined by silver nitrate titration. Moreover, ammonia dissolved in water and unreacted formamide were determined by ion chromatography and gas chromatography, respectively. As a result, the conversion of formamide was 99.5%, the yield of prussic acid was 95.2%, and the yield of ammonia was 4.3%.

EXAMPLE 17

Lactide Synthesis 4 from DL-methyl Lactate Material by Addition of Methyl Orthoformate The operation of reaction was conducted by the same procedure as in Example 1 except that DL-methyl lactate obtained by carrying out the above-mentioned synthetic examples plural times was used as DL-methyl lactate in the step (1) of Example 1, thereby obtaining 214.2 g of lactide. The thus obtained lactide had a purity of 99.6% (mesolactide=41.3%, DL-lactide=58.3%), an acid value of 4.8 meq/kg and a water content of 15 ppm.

What is claimed is:

1. A process to prepare a cyclic ester product comprising heating a reaction mixture comprising an α-hydroxycarboxyliclic acid or an α-hydroxycarboxylic acid ester represented by the formula $R^1R^2C(OH)COOR^3$, wherein $R^1$, $R^2$ and $R^3$ are each a hydrogen atom or an alkyl group having 1 to 6 carbon atoms, or a mixture of said α-hydroxycarboxylic acid and said α-hydroxycarboxylic acid ester as a raw material, wherein at least one orthoester is added to the raw material before the heating, or to the reaction mixture during the heating or after completion of the heating, said at least one orthoester being represented by the formula (I)

$$R^4C(OR^5)_3 \qquad (I)$$

wherein $R^4$ is a hydrogen atom or an alkyl group having 1 to 6 carbon atoms, each $R^5$ is an alkyl group having 1 to 6 carbon atoms, and each $R^5$ is the same or different.

2. The process according to claim 1 wherein an acid and water are present in at least one of the raw material, the reaction mixture or the cyclic ester product, and are converted into an alcohol and an ester with the orthoester, and the thus formed alcohol and ester are then removed.

3. The process according to claim 2 wherein the formed alcohol and ester are removed by distillation.

4. The process according to claim 1 wherein the orthoester is a compound selected from the group consisting of methyl orthoformate, ethyl orthoformate, methyl orthoacetate and ethyl orthoacetate.

5. The process according to claim 1 wherein the α-hydroxycarboxyliclic acid or the α-hydroxycarboxyliclic acid ester as the raw material is lactic acid or a lactic acid ester, and the cyclic ester is a lactide.

6. The process according to claim 5 wherein the lactic acid ester is obtained by (A) producing lactonitrile from prussic acid and acetaldehyde, (B) hydrating lactonitrile obtained by the previous step (A) to form lactamide, (C) forming the lactic acid ester and formamide from lactamide obtained by the previous step (B) and a formic acid ester of the formula HCOOR, wherein R is an alkyl group having 1 to 6 carbons, and (D) separating formamide from the products obtained in the previous step (C), dehydrating the formamide to form prussic acid, and recycling the formed prussic acid.

7. The process according to claim 5 wherein the lactic acid ester is methyl lactate, and the cyclic ester is a lactide.

8. The process according to claim 1 wherein the α-hydroxycarboxyliclic acid or the α-hydroxycarboxyliclic acid ester as the raw material is a α-hydroxyisobutylic acid or methyl α-hydroxyisobutylate, and the cyclic ester is tetramethyl glycolide.

9. A process to purify a cyclic ester product containing a cyclic ester, and water and an acid asL( impurities, which comprises adding at least one orthoester represented by the formula (I)

$$R^4C(OR^5)_3 \qquad (I)$$

wherein $R^4$ is a hydrogen atom or an alkyl group having 1 to 6 carbon atoms, each $R^5$ is an alkyl group having 1 to 6 carbon atoms, and each $R^5$ is the same or different, to a cyclic ester obtained by heating a reaction mixture comprising an α-hydroxycarboxylic acid or an α-hydroxycarboxyliclic acid ester represented by the formula $R^1R^2C(OH)COOR^3$, wherein $R^1$, and $R^3$ are each a hydrogen atom or an alkyl group having 1 to 6 carbon atoms, or a mixture of said α-hydroxycarboxylic acid and said α-hydrocarboxylic acid ester as a raw material, to convert the acid and water present in the cyclic ester product into, respectively, an alcohol and an ester, and moving the formed alcohol and ester.

10. The process according to claim 1 wherein the α-hydrocarboxylic acid is selected from the group consisting of glycolic acid, lactic acid and α-hydroxyisobutylic acid; and the α-hydroxycarboxyliclic acid ester is selected from the group consisting of methyl glycolate, ethyl glycolate, methyl lactate, ethyl lactate, butyl lactate, methyl α-hydroxyisobutylateand ethyl α-hydroxyisobutylate.

11. The process according to claim 10 wherein the orthoester is selected from the group consisting of methyl orthoformate, ethyl orthoformate, propyl orthoformate, methyl orthoacetate, ethyl orthoacetate, propyl orthoacetate, methyl orthopropionate, ethyl orthopropionate, methyl orthoisopropionate, ethyl orthoisopropionate, methyl orthobutylate, ethyl orthobutylate, methyl orthoisobutylate and ethyl orthoisobutylate.

12. The process according to claim 1 wherein the orthoester is in an amount of 0.5 to 10 equivalents of a total value of an acid value and a water content of the raw material, as defined by the following equation: total value=acid value in meq/kg+water content in (ppm/18).

13. The process according to claim 12 wherein the orthoester is in an amount of 1 to 5 equivalents of the total value.

14. The process according to claim 13 wherein the process is carried out at a temperature of 25 to 300° C.

15. The process according to claim 14 wherein the temperature is 50 to 250° C.

16. The process according to claim 14 wherein the temperature is 100 to 200° C.

17. The process according to claim 16 wherein the heating is carried out for a time of 0.1 to 10 hours.

18. The process according to claim 17 wherein the time is 0.2 to 5 hours.

19. The process according to claim 17 wherein the time is 0.5 to 2 hours.

* * * * *